United States Patent
Kindlein et al.

(10) Patent No.: US 7,749,150 B2
(45) Date of Patent: Jul. 6, 2010

(54) DEVICE FOR RADIATION TREATMENT OF PROLIFERATIVE TISSUE SURROUNDING A CAVITY IN AN ANIMAL BODY

(75) Inventors: Johann Kindlein, Toenisvorst (DE); Hans Martin Schot, Veenendaal (NL)

(73) Assignee: Nucletron B.V., Veenendaal (NL)

( * ) Notice: Subject to any disclaimer, the term of this patent is extended or adjusted under 35 U.S.C. 154(b) by 1212 days.

(21) Appl. No.: 11/165,128

(22) Filed: Jun. 24, 2005

(65) Prior Publication Data

US 2006/0015166 A1      Jan. 19, 2006

(30) Foreign Application Priority Data

Jul. 15, 2004   (EP) .................... 04077042

(51) Int. Cl.
*A61N 5/00* (2006.01)
(52) U.S. Cl. .......................................................... 600/3
(58) Field of Classification Search .................. 600/1–8
See application file for complete search history.

(56) References Cited

U.S. PATENT DOCUMENTS

| | | | | |
|---|---|---|---|---|
| 4,584,991 | A | * | 4/1986 | Tokita et al. ............... 600/3 |
| 4,763,642 | A | * | 8/1988 | Horowitz .................... 600/7 |
| 4,891,165 | A | * | 1/1990 | Suthanthiran .............. 600/8 |
| 4,976,680 | A | * | 12/1990 | Hayman et al. ............ 600/7 |
| 5,084,001 | A | * | 1/1992 | Van't Hooft et al. ........ 600/3 |
| 5,913,813 | A | * | 6/1999 | Williams et al. ............ 600/3 |
| 6,083,148 | A | | 7/2000 | Williams |
| 6,251,060 | B1 | * | 6/2001 | Hooft et al. ................ 600/3 |
| 6,264,599 | B1 | * | 7/2001 | Slater et al. ................ 600/7 |
| 6,575,888 | B2 | * | 6/2003 | Zamora et al. ............. 600/3 |
| 6,638,308 | B2 | * | 10/2003 | Corbitt et al. .............. 623/8 |
| 7,267,643 | B2 | * | 9/2007 | Koster et al. ............... 600/7 |
| 2003/0181782 | A1 | * | 9/2003 | McDaniel .................. 600/3 |
| 2005/0070753 | A1 | * | 3/2005 | Forman et al. ............. 600/3 |

FOREIGN PATENT DOCUMENTS

| | | |
|---|---|---|
| EP | 1402922 A1 | 3/2004 |
| WO | WO-02/092162 A2 | 11/2002 |

* cited by examiner

*Primary Examiner*—Samuel G Gilbert
(74) *Attorney, Agent, or Firm*—Birch, Stewart, Kolasch & Birch, LLP

(57) ABSTRACT

The invention relates to a device for radiation treatment of proliferative tissue surrounding a cavity in an animal body comprising a radiation delivering means for placing at least one energy emitting source at a desired position within the cavity for performing radiation treatment. The device includes at least one permanent implant element for placement in the body cavity that is made from a non-deformable material and has an outer surface around which the inner surface of the body cavity will adapt or conform itself. The invention aims to provide a device and method for radiation treatment of proliferative tissue surrounding a cavity in an animal body, wherein the radiation treatment is performed in a far more accurate and reproducible manner and wherein the device causes far less discomfort to the patient.

25 Claims, 11 Drawing Sheets

DEVICE FOR RADIATION TREATMENT OF PROLIFERATIVE TISSUE SURROUNDING A CAVITY IN AN ANIMAL BODY

BRIEF SUMMARY OF THE INVENTION

The invention relates to a device for radiation treatment of proliferative tissue surrounding a cavity in an animal body comprising radiation delivering means for placing at least one energy emitting source at a desired position within said cavity for performing said radiation treatment.

The invention also relates to an implant element to be implanted into a cavity in an animal body for radiation treatment of proliferative tissue surrounding said cavity.

The invention also relates to a method for performing radiation treatment of proliferative tissue surrounding a cavity in an animal body comprising the steps of:

A removing in a first surgical step a tumour from said animal body thereby creating said cavity;
B placing a brachytherapy applicator within said cavity;
C inserting at least one energy emitting source in said brachytherapy applicator at a desired position relative to said cavity for performing said radiation treatment;
D after a predetermined time removing said at least one energy emitting source after performing said radiation treatment.

A device according to the preamble is also indicated as a brachytherapy applicator and is for example known from the U.S. Pat. No. 5,492,582. In U.S. Pat. No. 5,492,582 a method and apparatus are described for treating tissue surrounding a surgically excised tumour with radioactive emission to kill any cancer cells that may be present in the margins surrounding the excised tumour. Following surgical removal of a tumour, say in the brain or breast, a supportive probe having an inflatable chamber connected at a distal end thereof is introduced into the cavity caused by the removal of the tumour.

A significant drawback of the known so-called "inflatable" devices is that the inflatable chamber or balloon is deformable adversely affecting the desired (read: correct) radiation dose distribution to the tissue to be treated.

Furthermore after the treatment the device is deflated and removed from the cavity of the patient. The removal of the device requires a second discomforting surgical procedure, which can be painful. Also the part of the device extending outside the patients body causes much discomfort to the patient in between subsequent treatment sessions.

The invention aims to obviate the above known drawbacks and to provide a device and method for radiation treatment of proliferative tissue surrounding a cavity in an animal body, wherein the radiation treatment is performed in a far more accurate and reproducible manner and wherein the device causes far less discomfort to the patient.

According to the invention said device comprises at least one permanent implant element for placement in said body cavity, said at least one element being made from a non-deformable material and having an outer surface being conformal to the inner surface of said body cavity.

Due to the permanent implant of the element into the cavity surrounding the tissue to be treated by radiation no discomfort is caused to the patient as subsequent removal and reintroduction in the cavity.

As the implant element is non-deformable and the outer surface has a shape/dimension that is conformal to that of the inner surface of the cavity (being the tissue layer to be treated) deformation of the surface of balloon system of the device is avoided and hence the radiation dose distributions will correspond with the intended, preplanned distribution and will be identical during subsequent treatment sessions.

According to an embodiment of the device according to the invention said non-deformable element is provided with at least one insertion hole for guiding said at least one energy emitting source inside said cavity. As stated above this will allow the positioning of an energy emitting source in an accurate, reproducible manner during subsequent treatment sessions improving the overall radiation treatment significantly.

More in particular said at least one insertion hole serves to accommodate a hollow guiding tube having a distal end to be inserted into said insertion hole and a proximal end remaining exposed outside said animal body.

An accurate positioning of the energy emitting sources within the cavity is further improved as according to the invention said device comprises fixating means for fixating said proximal end of said guiding tube relative to said animal body.

The device may also comprise further fixating means for fixating the device inside the cavity to the tissue surrounding the cavity. This latter fixating step is performed following surgical removal of the tumour.

According to the invention the device is further characterized in that said at least one guiding tube serves to accommodate a hollow catheter tube having a distal end to be inserted into said guiding tube and a proximal end to be connected to an afterloader apparatus, wherein moreover said at least one energy emitting source is contained in said afterloader apparatus and guided through said hollow catheter tube toward said cavity using a source wire having a distal end connected to said energy emitting source.

According to a embodiment of the implantable element said element consists of an outer shell part surrounding an inner core part. In one preferred embodiment at least said inner core part is manufactured from a non-absorbable, biocompatible material, for example from a filling material, for example from expandable poly-vinyl-alcohol (PVA), poly-ethylene-glycol, a saline solution, silicone gel or stabilized semisolid fibrin.

In another embodiment said outer shell part can be made from a resilient material, for example from silicon.

In yet another embodiment said outer shell part and/or inner core part of said non-absorbable, bio-compatible element can be manufactured from a porous poly-ethylene material and more in particular from expanded polytetra-fluoroethylene (e-PTEE).

The implant elements made from such porous poly-ethylene material are flexible and soft. It is also possible to use as a material a "mesh structure" commercially available by Atrium Medical Corporation. The implant element made from a porous material encourages the body's tissue to grow into the implant element thereby improving the recovery of the patient. Moreover the need for a second painful, discomforting surgery procedure in order to remove the implant element after treatment is herewith obviated.

Another embodiment of the element according to invention is characterized in that at least said outer shell part is manufactured from a bio-absorbable material, for example from poly-lactide, wherein the inner core part is made from one of the materials listed above. In this embodiment the outer shell part is allowed to be absorbed by the patient's body, whereas a non-absorbable, bio-compatible inner core part remains inside the patient's body. In the case of an inner core part of a porous material like stabilized semisolid fibrin of a porous material, like poly-ethylene the body's tissue grow into the implant element is encouraged.

Also both the outer shell part and inner core part can be made from a bio-absorbable material. In this latter example the whole element is allowed to be absorbed by the patients body after treatment leaving no non-body materials behind in the patient.

A specific embodiment of the element according to the invention consists of an outer shell part surrounding an inner open core part.

Both the bio-absorbable and the non-absorbable, bio-compatible implant element may in a specific embodiment consist of at least two separate interconnected element parts, this in order to facilitate the implant of the element in the cavity to be treated. In a specific embodiment said implant element parts may be semi-spherical or ovoid.

Furthermore said separate element parts are each provided with cooperating connection means, wherein said connection means may comprise multiple protrusions and corresponding openings provided on said element parts. This guarantees the preservation of the outer dimensions of the implant element after implant within the cavity even during subsequent radiation treatment, thereby maintaining a reproducible radiation dose distribution.

According to another, beneficial embodiment according to the invention said device is composed from two or more permanent implant elements, which two or more permanent implant elements are interconnected to each other using interconnecting means.

Said interconnecting means may comprise elongated shaped interconnecting elements having a first and second end, which first and second ends fit in corresponding openings present in the outer surface of said permanent implant elements.

According to one embodiment said elongated shaped interconnecting elements exhibit a straight configuration, whereas in another embodiment said elongated shaped interconnecting elements exhibit a bent configuration, for example shaped as a 90° degree arc.

The method according to the invention is further characterized in that step B consists of the step of E positioning an implant element according to anyone of the preceding claims into said cavity; and F leaving said implant element into said cavity after performing step C.

The guiding tubes, which to be inserted into the insertion holes of the permanent implant element can be likewise be manufactured from one of said non-absorbable, bio-compatible materials mentioned above. The guiding tubes can also be manufactured from a bio-absorbable material, for example from poly-lactide.

BRIEF DESCRIPTION OF THE DRAWINGS

The invention will be now described with reference to the accompanying drawings, which drawings show in.

For the sake of clarity the corresponding parts in the different embodiments will be denoted with identical reference numerals.

DETAILED DESCRIPTION OF THE INVENTION

Figure 1A:
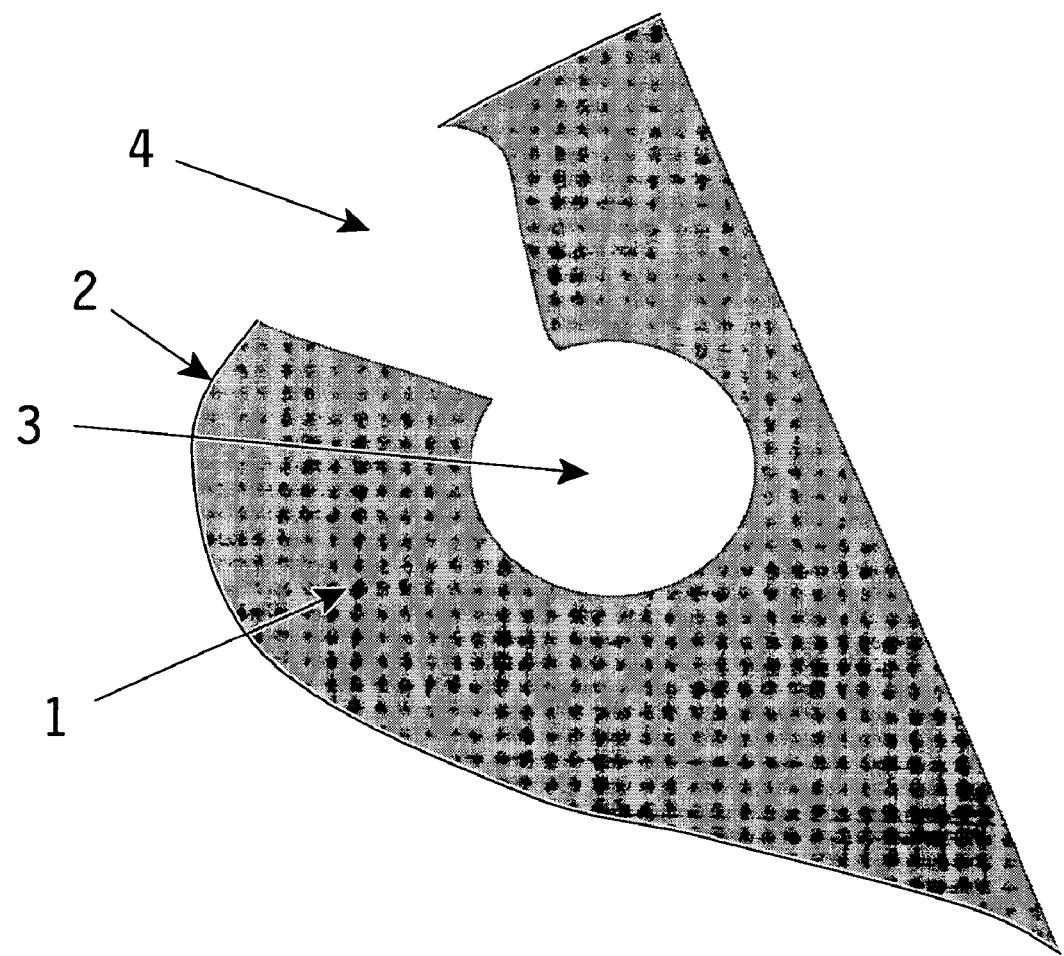
FIGS. 1a-1d a first embodiment of a device according to the invention shown in subsequent steps of the method according to the invention.
Figure 1B:
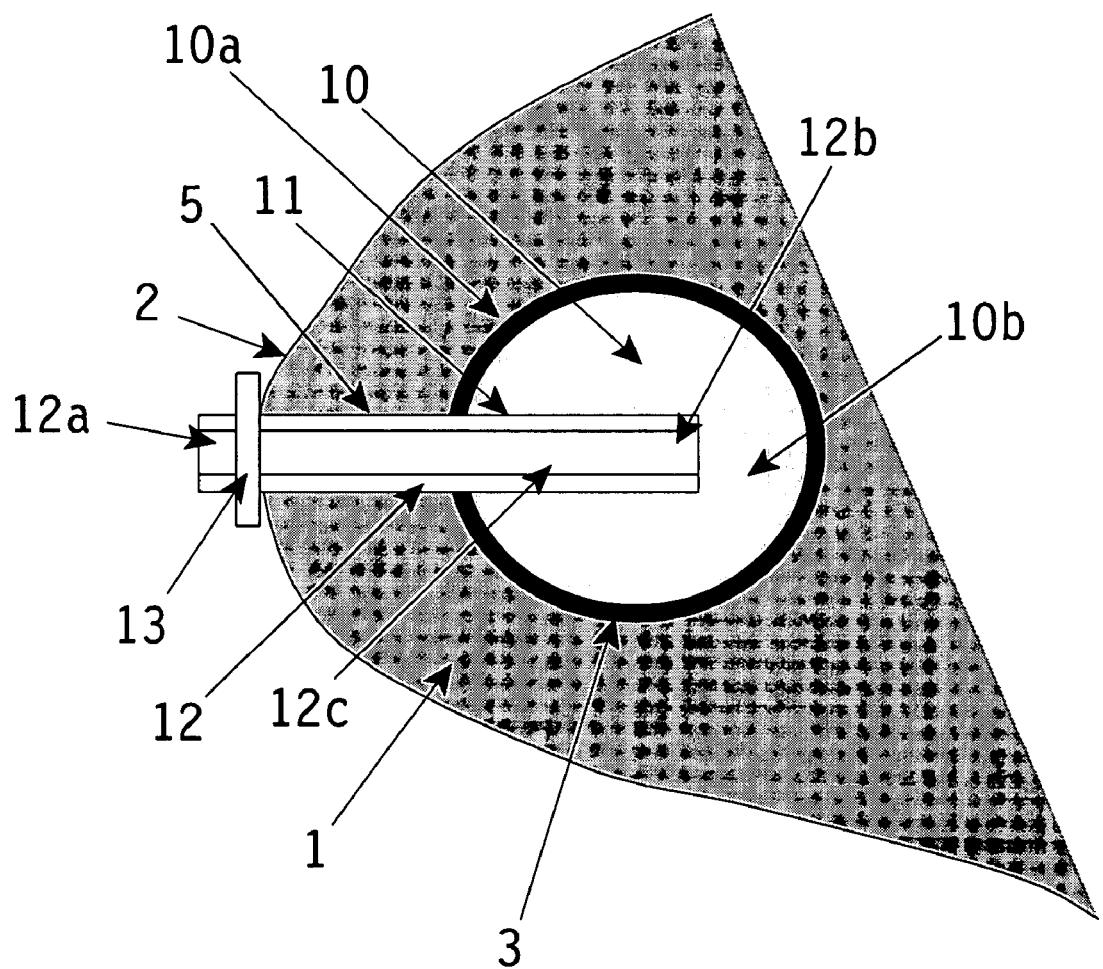

FIGS. 1a-1b disclose a first embodiment of the device according to the invention as shown in subsequent steps of the method according to the invention.

The device and method according to the invention will now be described by means of the radiation treatment of proliferative tissue surrounding a cancer tumour for example in a women's breast.

In an known first step of the method according to the prior art the cancer tumour is removed by surgery from the patient's body (the women's breast 1) thereby creating a surgical incision wound 4 and a cavity 3 where the tumour is excised from (FIG. 1a). In the next step of the method according to the invention a non-deformable element 10 is placed via said surgical incision wound 4 into said body cavity 3 after which the surgical incision wound 4 is closed. The implant element 10 being part of the device according to the invention is intended for permanent placement in the patient's body 1 and is made of a non-deformable material containing an outer surface 10a being conformal to the inner surface of the body cavity 3.

As shown in FIG. 1b said non-deformable element 10 is provided with at least one insertion hole 11, which serves to accommodate a hollow guiding tube 12. The hollow guiding tube 12 exhibits a distal end 12b for insertion into said insertion hole 11 and a proximal end 12a which remains exposed outside the patient's body 1.

As the implant element 10 is made of a non-deformable material an exact orientation of the guiding tube 12 in the corresponding insertion hole 11 is accurately maintained. The accurate position or orientation of the hollow guiding tube 12 within the insertion hole 11 of the implant element 10 is further assured as according to the invention the device comprises fixating means 13 for fixating the proximal end 12a of the guiding tube 12 relative to the skin 2 of the patient's body 1. The fixating means 13 may comprise a clamping element, which clamping element, after shifting it over the proximal end 12a against the skin surface 2, can be clammed against the circumferential surface of the proximal end 12a. The clamping element 13 can also be adhered against the skin surface 2 using a glue or adhesive film.

All guiding tubes 12 to be used with the intended radiation treatment are placed in the corresponding insertion holes 11 present in the outer surface 10a of the permanent implant element 10 prior to the implant of said implant element 10 in said body cavity. Hence once the cancer tumour is removed by surgery from the patient's body (the women's breast 1) the assembly of permanent implant element 10 with pre-positioned guiding tubes 12 is placed via the surgical incision wound 4 into the body cavity 3 where the tumour is excised from (see FIG. 1a).

The proximal ends 12a of each guiding tube 12 remain exposed outside the patient's body 1 once the surgical incision wound 4 is closed. Subsequently one or more hollow catheter tubes 19 are inserted with their distal end 19b via the proximal end 12a of a corresponding guiding tube 12 until said distal end 19b reaches the distal end 12b of the guiding tube 12. This situation is depicted in FIG. 1c.

Figure 1C:
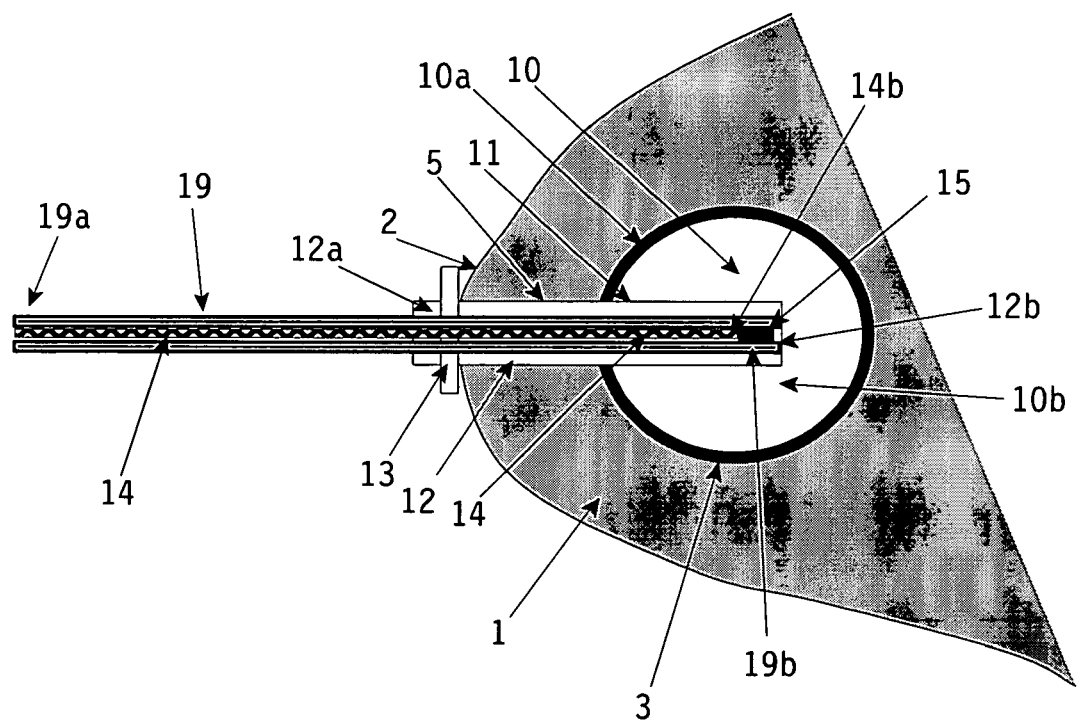

Each hollow catheter tube 19 comprises also a proximal end 19a, which is to be connected to an after loader apparatus (not shown in FIG. 1c). For performing the radiation treatment of the proliferative tissue now surrounding the implant element 10 a source wire 14 is advanced from said after loader apparatus through the hollow catheter tube 19 and the hollow guiding tube 12 towards the distal end 12*b* thereof within the implant element 10. See again FIG. 1*c*.

An energy emitting source 15 is connected to the distal end 14*b* of the source wire 14 and is advanced by said source wire 14 from the after loader apparatus until within the implant element 10. The energy emitting source may be a radioactive source emitting radiation according to a natural decay sequence. However the energy emitting source 15 can also be a High Dose Rate or Pulse Dose Rate source, for example an Ir-192 source. The energy emitting source can also be a miniature X-ray source.

Once the radiation treatment session has been performed after a specific preplanned time the source wire 14 is retracted together with the energy emitting source 15 through the hollow guiding tube 12 and the hollow catheter tube 19 back into the after loader apparatus. The hollow catheter tube(s) 19 is (are) then also retracted from the guiding tube(s) 12.

The guiding tube 12 remains within the patient's body and the implant element 10 in between subsequent radiation treatment sessions and during that prolonged period of time the patient is allowed to move freely, even outside the hospital, whereas the guiding tube 12 remains within the implant element 10. As the guiding tube 12 is fixed by means of the fixating means 13 to the skin 2 of the patient an accurate and reproducible orientation of the guiding tube 12 relative to the patient's body is maintained, allowing subsequent radiation treatment sessions to be performed. As the patient is allowed to move freely between subsequent radiation treatments, even outside the hospital the implant element 10 within the cavity of the patient's body and the guiding tube 12 being exposed outside the patient's body 1 discomforts the patient to a minimum.

As the repositioning of the energy emitting source can be accurately reproduced identical subsequent radiation treatment sessions can be performed, resulting in a very precise overall radiation treatment where the actual radiation dose being administrated accurately conforms the desired, pre-planned radiation dose.

Figure 1D:
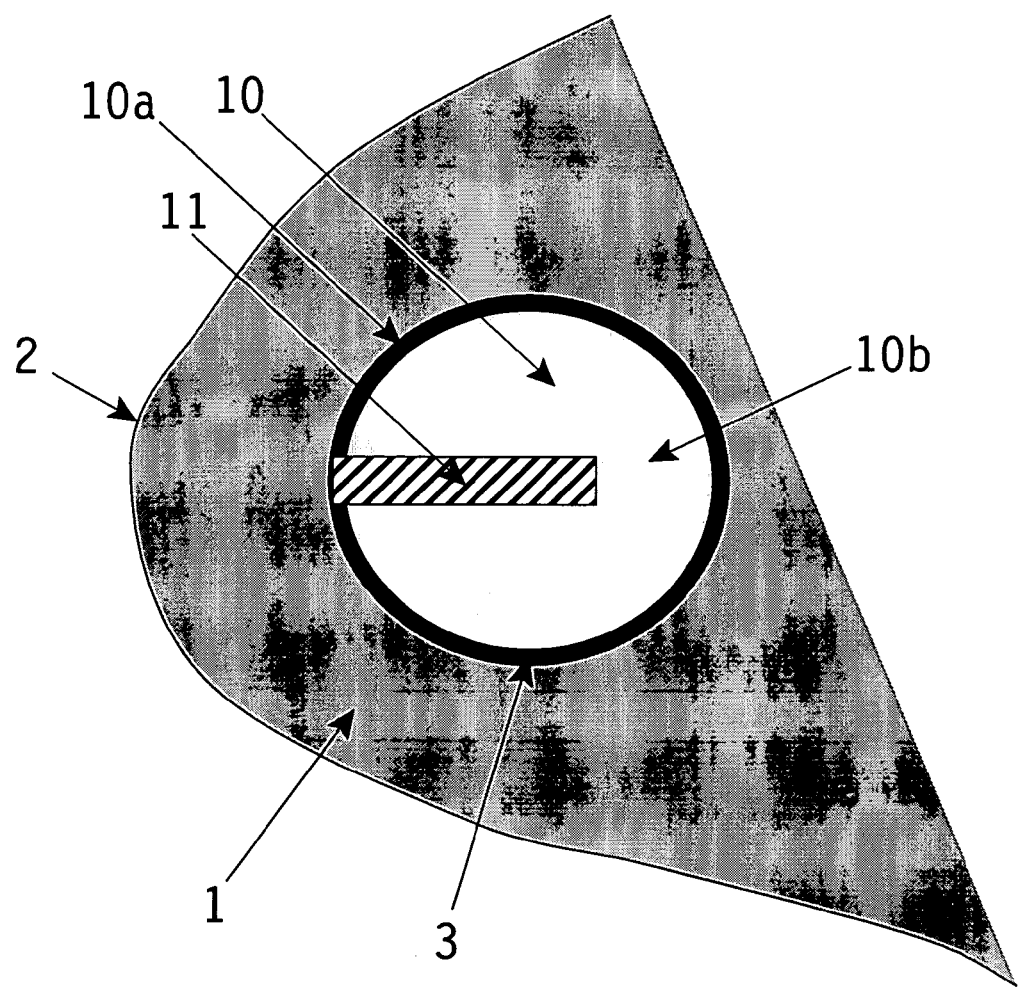

Once the overall radiation treatment has been performed the guiding tube 12 is removed from the implant element 10 and the implant element 10 together with the empty insertion hole 11 remains within the body cavity 3. Once the insertion wound created by the guiding tube 12 is healed the presence of the implant element 10 will become invisible from the outside. This stage of the method step according to the invention is shown in FIG. 1*d*.

FIGS. 1*a*-1*d* also disclose a specific embodiment of the implant element 10 according to the invention. The implant element 10 is composed of an outer shell part 10*a* surrounding an inner core part 10*b*. Preferably the outer shell part is made from a resilient material, for example from silicon, whereas the inner core part is made from a filling material, for example from expandable poly-vinyl-alcohol (PVA), poly-ethylene-glycol, a saline solution, silicone gel.

In another embodiment the implant element 10 is manufactured from a bio-absorbable material, for example from poly-lactide. Once the radiation treatment has been performed and the implant element 10 is left inside the patient's body 1, the element 10 being made from poly-lactide will be gradually absorbed by the patient's body until the whole implant element has disappeared.

Figure 2A:
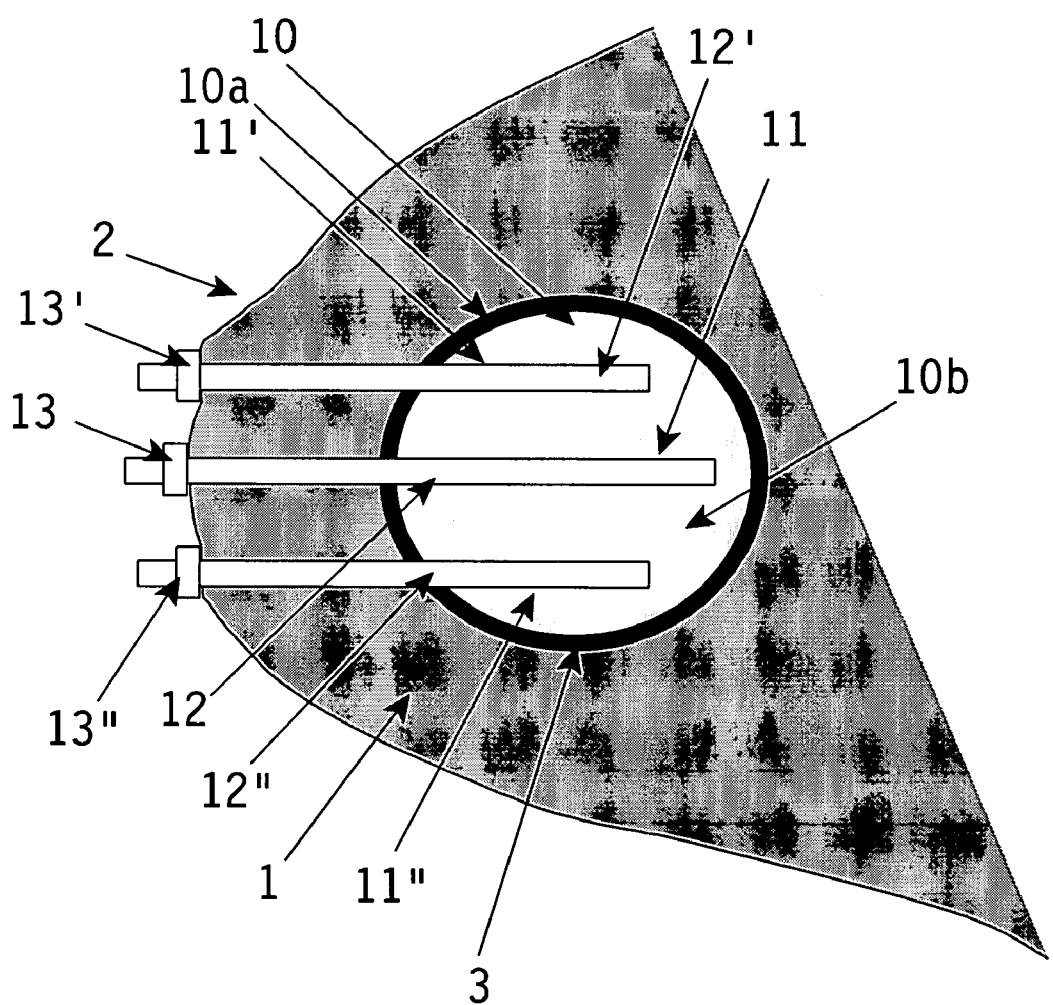
FIGS. 2a-2b a second embodiment of a device according to the invention.

In the embodiment of FIG. 2*a* the implant element 10 is provided with multiple insertion holes 11-11'-11" for accommodating corresponding hollow guiding tubes 12-12'-12". Also in the embodiment as shown in FIG. 2*a* each guiding tube 12-12'-12" is fixated to the skin 2 of the patient's body 1 by using suitable fixating means 13-13'-13".

As stated above it is preferred to place the assembly of permanent implant element 10 with pre-positioned guiding tubes 12 via the surgical incision wound 4 into the body cavity 3 where the tumour is excised from (see FIG. 1*a*).

Figure 2B:
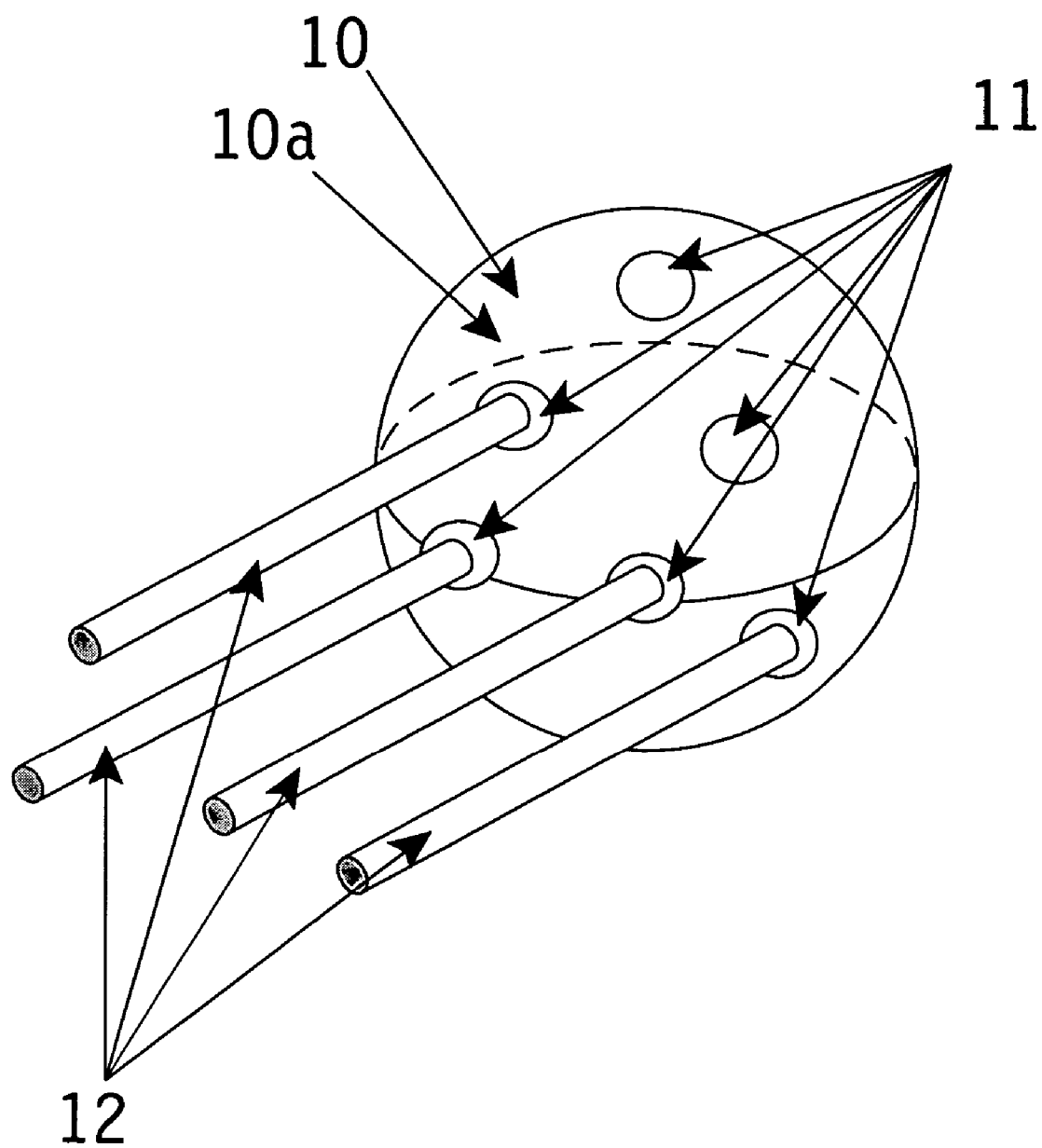

According to the invention and as shown in FIG. 2*b* the implant element 10 has a spherical shape with one or more insertion holes 11 present in the surface 10*a* and extending until the interior of the implant element 10. Into the insertion holes 11 corresponding guiding tubes 12 are to be inserted.

Figure 3A:
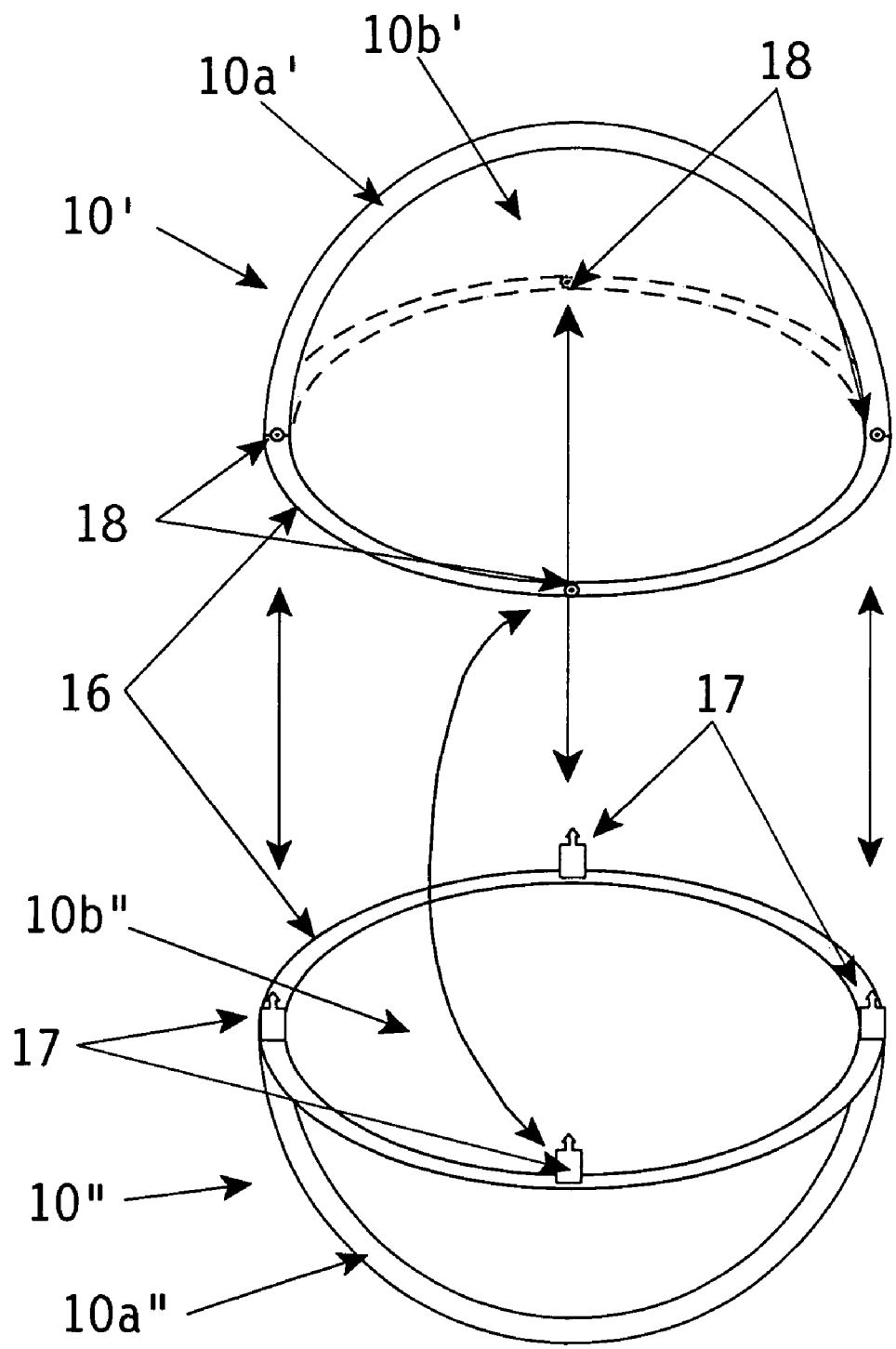
FIGS. 3a-3b a third and fourth embodiment of a device according to the invention.
Figure 3B:
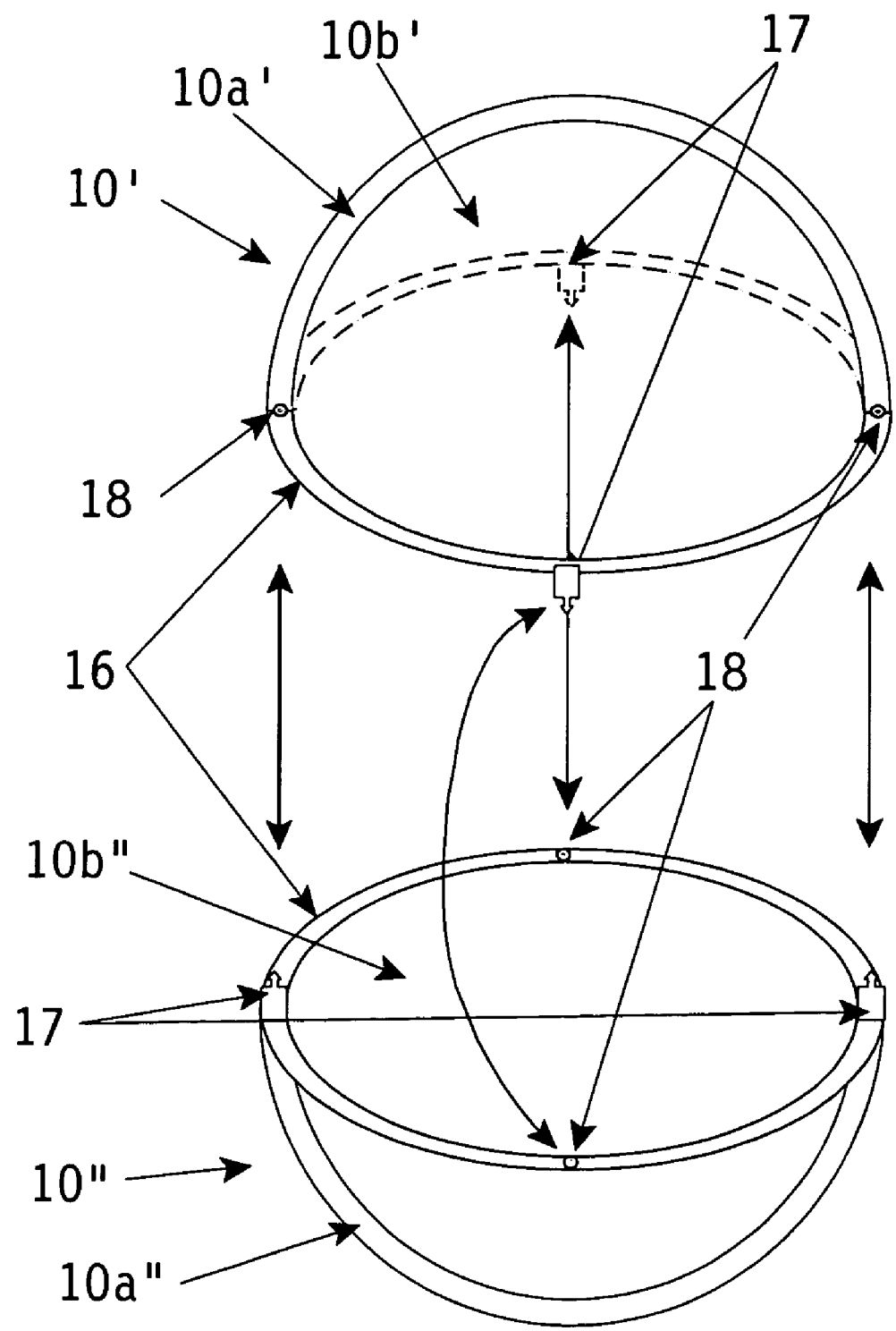

An advantageous embodiment of the implant element 10 according to the invention is shown in FIGS. 3*a* and 3*b*, wherein the implant element 10 is composed of two more or less identical parts 10'-10", which element parts are constructed as semi-sphericals. Each element part 10'-10" comprises a surface or outer shell part 10*a*'-10*a*" and an open inner core part 10*b*'-10*b*" (hence where no implant element material is present).

However the element parts 10'-10" can also exhibit other spatial shapes, like an ovoid shape or other geometrical shapes.

Additionally the outer surface of the element parts 10'-10" can be perforated or otherwise be provided with holes.

The separate semi-spherical element parts 10'-10" allows an easy insertion into the cavity 3 via the surgical incision wound 4 as created in order to remove the cancerous tumour from the patient's body 1 (see FIG. 1*a*). In order to compose the implant element 10 from both implant parts 10'-10", both semi-spherical element parts are provided with a circular contact surface 16. When the implant element 10 is composed of both element parts 10'-10" both element parts abut against each other a long said contact surfaces 16. In order to maintain the abutment of both element parts 10'-10" both abutment surfaces 16 are provided with interacting connection means 17-18.

FIG. 3*a* shown a first embodiment of said connection means, wherein the first element part 10' is provided with multiple openings 18 present within said abutment surface 16, whereas the other implant element 10" is provided with corresponding protrusions 17 which are also present on the abutment surface 16. When composing the implant element 10 from both element parts 10'-10" the protrusions 17 fit in said corresponding openings 18 and the connection between both element parts 10'-10" is assured as the protrusions 17 are provided with a click mechanism preventing an unintentional and undesired detachment of both element parts 10'-10" for example due to abrupt movements of the patient's body or impacts on said patient's body.

Another embodiment as shown in FIG. 3*b* discloses two element parts 10'-10" which are identical as they both comprise openings 18 and protrusions 17 which engage with each other when both element parts 10'-10" are placed against each other.

Figure 4A:
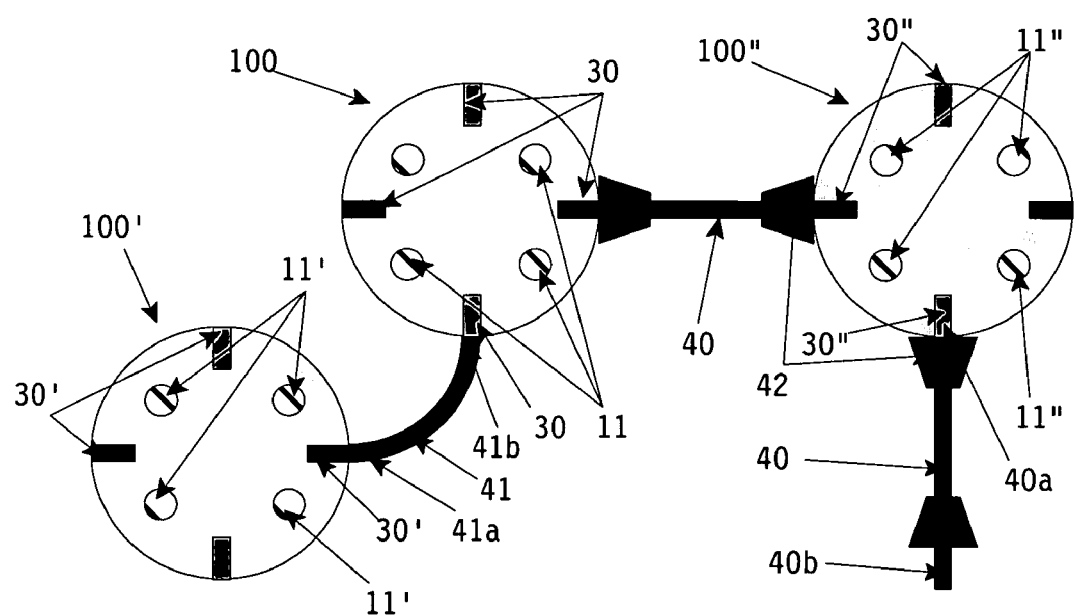
FIG. 4 a fifth embodiment of a device according to the invention.
Figure 4B:
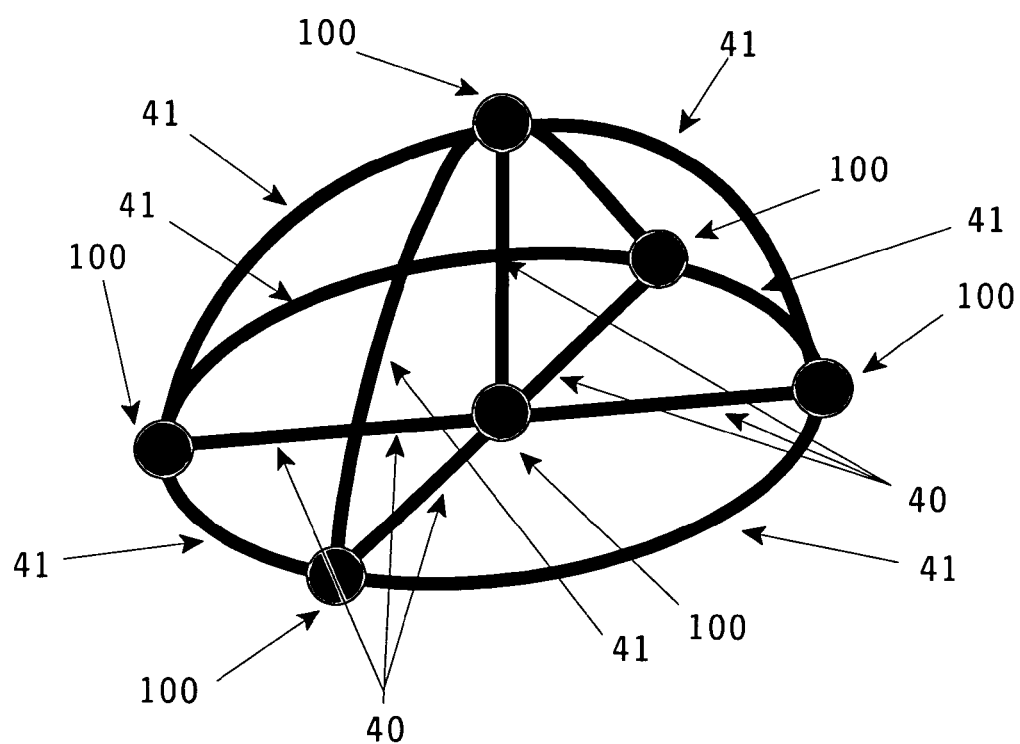

FIGS. 4*a*-4*b* disclose other embodiments of the device according to the invention. In FIGS. 4*a*-4*b* the device is composed as a kit-assembly of a plurality (two or more) permanent implant elements 100-100'-100"-etc. The kit-assembly of multiple permanent implant elements 100-100'-100"-etc. are interconnected with each other by means of interconnecting means 40-41-42. The interconnecting means comprise different elongated shaped interconnection elements 40-41, each having a first and a second end 40*a*-40*b* respectively 41*a*-41*b*, which first and second ends fit in corresponding openings 30-30'-30" present in the outer surface of said permanent implant elements 100-100'-100".

As depicted in FIG. 4a, one embodiment of said elongated shaped interconnecting elements exhibit a straight configuration and is depicted with reference numeral 40. Another embodiment of the elongated shaped interconnecting elements exhibit a bent configuration and more particular said bent shaped interconnecting element 41 is shaped as an arc of 90°. When fitting multiple permanent implant elements 100-100'-100"-etc. any three dimensional configuration can be constructed using the interconnecting means 40 (straight) or 41 (90° degree arc). The three dimensional shaped constructions using multiple permanent implant elements can be spheres, cylinders or other angular geometrical shapes.

Like the permanent implant devices also the interconnecting elements 40-41 can be manufactured from bio-compatible, non-absorbable materials or from bio-absorbable materials as discussed in this application.

Using suitable fixation elements 42 the interconnecting elements 40-41 can be held in place when inserted into the connecting openings 30-30'-30" present in the permanent implant elements 100-100'-100". As each permanent implant element 100-100'-100" is provided with one or more insertion holes 11-11'-11" in which the guiding tubes 12 (not depicted) are to be inserted a well defined three dimensional orientation of the positions where the energy emitting sources are to be placed (using the catheter tubes and the source wires as discussed previously in this application) can be obtained depending on the radiation therapy treatment to be performed on the proliferative tissue surrounding the cavity.

Preferably each permanent implant element 100-100'-100" is in this specific three-dimensional constructional embodiment shaped as a sphere and provided with 1-6 openings or holes 30-30'-30" located at certain angles on the outer surface of the permanent implant elements 100-100'-100" in order to allow the unambiguous construction of variable three dimensional geometries like letters structures, or imitations of carbon allotropes, like diamond, graphite, buckeyballs, buckeytubes, etc.

An example of a kit-assembly of the device according to the invention is disclosed in FIG. 4b, wherein multiple implant elements 100 are interconnected with the use of straight interconnecting elements 40 and 90° arc-shaped interconnecting elements 41, thus creating a spherical assembly of an implant device according to the invention.

Likewise, the guiding tubes 12, which to be inserted into the insertion holes 11 of the permanent implant element 10 according to the invention can be likewise be manufactured from one of said non-absorbable, bio-compatible materials mentioned above. The guiding tubes 12 can also be manufactured from a bio-absorbable material, for example from polylactide.

Besides eliminating the need for a second, painful, discomforting surgical procedure (for removing the implant element after treatment) the use of the bio-degradable or bio-absorbable materials offers other advantages. The use of bio-degradable polymers for manufacturing the implant element 10 (and the guiding tubes 12) stimulates tissue growth around the implant element after placement into the body cavity. The bio-degradable polymers exhibit a certain degree of porosity and form a matrix on which the cell growth of the tissue surrounding the implanted elements and guiding tubes is stimulated. The polymer matrix may represent the device itself, and it serves also as a "scaffold" for cell growth.

Also the use of non-absorbable but bio-compatible materials especially expanded polytetrafluro-ethylene (e-PTFE) stimulate tissue growth around, but especially inside the implant elements. These implants are flexible and soft. The implants are thin-walled tubes consisting of a soft, high-porosity center that is surrounded by a smooth medium porosity outer layer. This tube shape encourages the body's tissue to grow into the implants.

Figure 5:
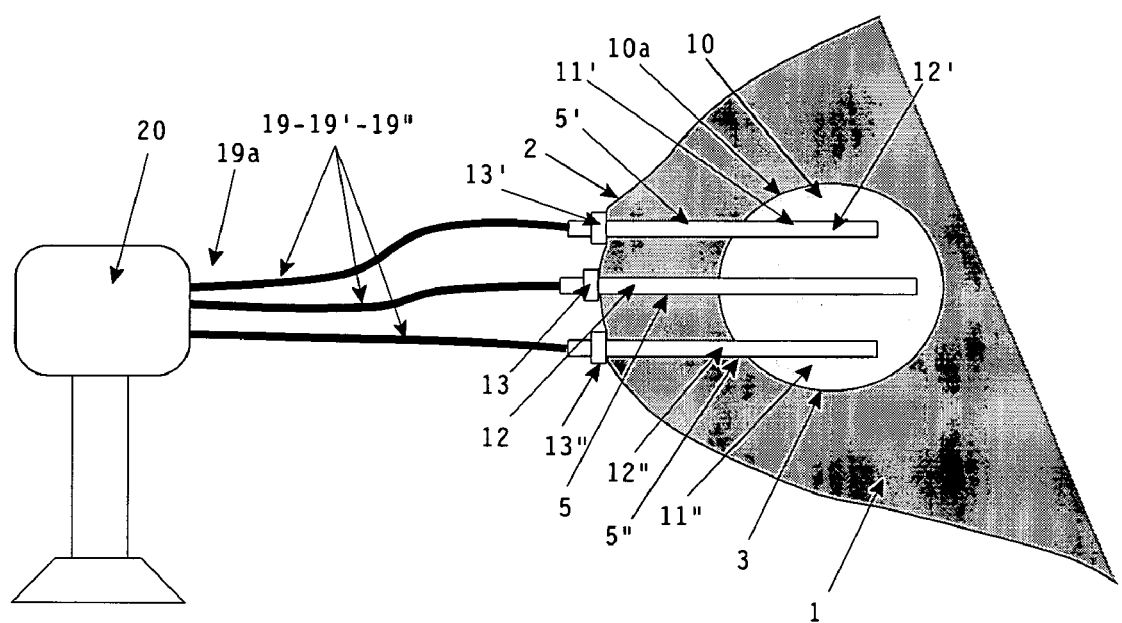
FIG. 5 an embodiment of a device according to the invention connected to an after loader device.

In FIG. 5 an application of the device according to the invention is disclosed wherein the implant element 10 is provided with three insertion holes 11'-11" in which corresponding guiding tubes 12'-12" are accommodated. To their proximal ends being exposed outside the patient's body 1 hollow catheter tubes 19 are connected with their proximal ends 19b, which catheter tubes 19 are connected to an after loader apparatus 20 with their proximal ends 19a.

As disclosed in FIG. 1c through said plurality of catheter tubes 19 a source wire 14 is advanced to which distal end 14b an energy emitting source 15 is connected. With the after loader apparatus 20 one or more energy emitting sources 15 can be advanced through the hollow catheter tubes 19-19'-19" and through the corresponding guiding tube 12-12'-12" towards different positions within the implant element 10 and relative to the proliferative tissue 3 to be treated by radiation and surrounding the implant element 10.

With the device according to the invention having multiple insertion holes 11-11'-11"-etc. it is possible to position several energy emitting sources 15 at the same time and at different locations within the implant element 10 and relative to the proliferative tissue 3 to be treated by radiation. The exact position of each energy emitting source in each guiding tube 12 relative to the proliferative tissue 3 is controlled by the after loader apparatus 20 based on a preplanned desired radiation dose distribution.

It is also possible to use one single energy emitting source which is advanced in succession through the several hollow catheter tubes 19-19'-19" towards different positions within the implant element 10. The position of the single energy emitting source within each insertion hole 11-11'-11"-etc. as well as its dwell time at said location is again controlled by the after loader apparatus 20 based on a radiation therapy preplan.

As the orientation of the implant element and the guiding tubes 12-12'-12" is maintained during the overall radiation treatment the single energy emitting source or multiple energy emitting sources are inserted in a reproducible manner into each guiding tube 12-12'-12" towards their desired position within the implant needle 10 during subsequent radiation treatment sessions, which are therefore identical, resulting in a very precise overall radiation treatment.

The invention claimed is:

1. A device for radiation treatment of proliferative tissue surrounding a cavity in an animal body comprising:
   a radiation delivering device comprising at least one removable energy emitting source at a desired position within said cavity for performing said radiation treatment, and
   at least one permanent implant element for placement in said body cavity, said at least one element comprising an inner core part made from a non-deformable material and having an outer surface around which the inner surface of said body cavity will adapt or conform itself, and being arranged to accommodate said at least one removable energy emitting source,
   wherein said permanent implant element comprises of at least two separate substantially identical interconnected element parts;
   wherein said element consists of an outer shell part surrounding said inner core part;
   wherein at least said inner core part is manufactured from a non-absorbable, bio-compatible material.

2. The device according to claim 1, wherein said permanent implant element is provided with at least one insertion hole for guiding and accommodating said at least one removable energy emitting source inside said cavity.

3. The device according to claim 2, further comprising a hollow guiding tube; wherein said at least one insertion hole serves to accommodate a hollow guiding tube having a distal end to be inserted into said insertion hole and a proximal end remaining exposed outside said animal body.

4. The device according to claim 3, wherein said device comprises a first fixating device configured to fixate said proximal end of said guiding tube relative to said animal body.

5. The device according to claim 3, wherein said hollow guiding tube being accommodated in said at least one insertion hole serves to accommodate a hollow catheter tube having a distal end to be inserted into said guiding tube and a proximal end to be connected to an afterloader apparatus.

6. The device according to claim 5, wherein said at least one energy emitting source is contained in said afterloader apparatus and guided through said hollow catheter tube toward said cavity using a source wire having a distal end connected to said energy emitting source.

7. The device according to claim 1, wherein at least said inner core part is made from a filling material.

8. The device according to claim 7, wherein said filling material is expandable poly-vinyl-alcohol (PVA), poly-ethylene-glycol, a saline solution, silicone gel or stabilized semi-solid fibrin.

9. The device according to claim 1, wherein said outer shell part is made from a resilient material.

10. The device according to claim 9, wherein said resilient material is silicon.

11. The device according to claim 1, wherein said outer shell part and/or inner core part of said non-absorbable, biocompatible element are manufactured from a porous polyethylene material.

12. The device according to claim 11, wherein said outer shell part and/or inner core part of said non-absorbable, biocompatible element are manufactured from expanded poly-tetra-fluoroethylene (e-PTEE).

13. The device according to claim 1, wherein at least said outer shell part is manufactured from a bio-absorbable material.

14. The device according to claim 13, wherein said bio-absorbable material is poly-lactide.

15. The device according to claim 1, wherein when assembled, said element parts are substantially spherical or ovoid.

16. The device according to claim 1, wherein said separate element parts are each provided with cooperating connectors.

17. The device according to claim 16, wherein said connectors comprise multiple protrusions and corresponding recesses provided on said element parts.

18. The device according to claim 1, wherein said device is built up as a kit-assembly composed from two or more permanent implant elements, which two or more permanent implant elements are interconnected to each other using an interconnecting device.

19. The device according to claim 18, wherein said interconnecting device comprises elongated shaped interconnecting elements having a first and second end, which first and second ends fit in corresponding openings present in the outer surface of said permanent implant elements.

20. The device according to claim 19, wherein said elongated shaped interconnecting elements exhibit a straight configuration.

21. The device according to claim 19, wherein said elongated shaped interconnecting elements exhibit a bent configuration.

22. The device according to claim 21, wherein said elongated shaped interconnecting elements are shaped as a 90 degree arc.

23. The device according to claim 1, wherein said inner core part is an open core part.

24. The device according to claim 1, wherein the device comprises further a fixating device configured to fixate the device inside the cavity to the tissue surrounding the cavity.

25. A method for performing radiation treatment of proliferative tissue surrounding a cavity in an animal body comprising the steps of:
A—removing in a first surgical step a tumour from said animal body thereby creating said cavity;
B—placing a brachytherapy applicator within said cavity;
C—inserting at least one energy emitting source in said brachytherapy applicator at a desired position relative to said cavity for performing said radiation treatment; and
D—after a predetermined time removing said at least one energy emitting source after performing said radiation treatment,
wherein step B further comprises the steps of:
E—positioning an implant element according to claim 1 into said cavity; and
F—leaving said implant element into said cavity after performing step C.

* * * * *